United States Patent
Collins

(10) Patent No.: US 10,207,034 B2
(45) Date of Patent: Feb. 19, 2019

(54) SLEEVES, MANIFOLDS, SYSTEMS, AND METHODS FOR APPLYING REDUCED PRESSURE TO A SUBCUTANEOUS TISSUE SITE

(71) Applicant: KCI Licensing, Inc., San Antonio, TX (US)

(72) Inventor: Barbara A. Collins, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 4 days.

(21) Appl. No.: 14/312,343

(22) Filed: Jun. 23, 2014

(65) Prior Publication Data

US 2014/0309602 A1 Oct. 16, 2014

Related U.S. Application Data

(62) Division of application No. 12/645,146, filed on Dec. 22, 2009, now Pat. No. 8,795,245.

(Continued)

(51) Int. Cl.
*A61M 1/00* (2006.01)
*A61M 25/00* (2006.01)

(52) U.S. Cl.
CPC ......... *A61M 1/0088* (2013.01); *A61M 1/0084* (2013.01); *A61M 25/003* (2013.01); *A61M 2025/0037* (2013.01)

(58) Field of Classification Search
USPC ........................................................ 604/319
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 3/1986
AU 745271 4/1999
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Tatyana Zalukaeva
*Assistant Examiner* — Guy K Townsend

(57) ABSTRACT

The illustrative embodiments described herein are directed to apparatuses, systems, and methods for applying reduced pressure to subcutaneous tissue site. In one illustrative embodiment, the apparatus includes a sleeve adapted for placement at a subcutaneous tissue site. The sleeve is further adapted to receive a manifold. The sleeve may also have an opening operable to transfer reduced pressure from the manifold to the subcutaneous tissue site. In one embodiment, the apparatus may also include a manifold that is insertable into the sleeve. The manifold may include at least one aperture, and may be operable to deliver reduced pressure to the subcutaneous tissue site via at least one aperture.

20 Claims, 6 Drawing Sheets

Related U.S. Application Data

(60) Provisional application No. 61/141,716, filed on Dec. 31, 2008.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flowers, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A * | 7/1983 | Muto | A61M 25/0111 128/DIG. 26 |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,721,123 A * | 1/1988 | Cosentino | A61M 25/002 134/113 |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A * | 1/1990 | Poirier | A61L 29/041 128/DIG. 26 |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A * | 9/1992 | Ferdman | A61M 1/0088 604/290 |
| 5,167,613 A | 12/1992 | Karami et al. | |
| 5,176,663 A | 1/1993 | Svedman et al. | |
| 5,215,522 A | 6/1993 | Page et al. | |
| 5,232,453 A * | 8/1993 | Plass | A61M 25/02 128/DIG. 26 |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A * | 10/1994 | Svedman | A61M 1/0088 604/175 |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,569,165 A * | 10/1996 | Chin | A61B 17/0218 294/81.3 |
| 5,607,388 A | 3/1997 | Ewall | |
| 5,636,643 A | 6/1997 | Argenta et al. | |
| 5,645,081 A | 7/1997 | Argenta et al. | |
| 5,749,826 A * | 5/1998 | Faulkner | A61F 2/0009 128/DIG. 25 |
| 5,785,706 A * | 7/1998 | Bednarek | A61M 25/0662 600/372 |
| 5,919,188 A * | 7/1999 | Shearon | A61B 18/1492 600/374 |
| 6,010,500 A * | 1/2000 | Sherman | A61B 18/1492 606/41 |
| 6,071,267 A | 6/2000 | Zamierowski | |
| 6,080,151 A * | 6/2000 | Swartz | A61B 18/1492 606/45 |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 6,936,037 B2 * | 8/2005 | Bubb | A61M 1/0088 601/6 |
| 7,235,070 B2 * | 6/2007 | Vanney | A61B 18/1492 606/41 |
| 2002/0077661 A1 * | 6/2002 | Saadat | A61B 17/08 606/221 |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2005/0055019 A1 * | 3/2005 | Skarda | A61B 18/1492 606/41 |
| 2006/0079852 A1 * | 4/2006 | Bubb | A61F 13/0203 604/317 |
| 2007/0005051 A1 * | 1/2007 | Kampa | A61B 18/1492 606/41 |
| 2007/0060935 A1 * | 3/2007 | Schwardt | A61B 17/22 606/170 |
| 2007/0219471 A1 * | 9/2007 | Johnson | A61B 17/88 601/6 |
| 2009/0306631 A1 * | 12/2009 | Santora | A61B 17/88 604/543 |
| 2010/0168692 A1 * | 7/2010 | Collins | A61M 1/0088 604/319 |
| 2012/0203144 A1 * | 8/2012 | Collins | A61D 9/00 601/6 |

FOREIGN PATENT DOCUMENTS

| | | |
|---|---|---|
| AU | 755496 | 2/2002 |
| CA | 2005436 | 6/1990 |

(56) References Cited

FOREIGN PATENT DOCUMENTS

| | | |
|---|---|---|
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 96/05873 | 2/1996 |
| WO | 97/18007 | 5/1997 |
| WO | 99/13793 | 3/1999 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Žirvadinovic, V. Ðukić, Ð. Maksimović, Ð. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, the Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

(56) References Cited

OTHER PUBLICATIONS

V.A.C.® Therapy Clinical Guidelines: A Reference Source for Clinicians (Jul. 2007).

* cited by examiner

SLEEVES, MANIFOLDS, SYSTEMS, AND METHODS FOR APPLYING REDUCED PRESSURE TO A SUBCUTANEOUS TISSUE SITE

CROSS-REFERENCE TO RELATED APPLICATIONS

This application is a Divisional of U.S. application Ser. No. 12/645,146, filed Dec. 22, 2009, which claims the benefit of U.S. Provisional Application No. 61/141,716, filed Dec. 31, 2008, which is hereby incorporated by reference.

BACKGROUND OF THE INVENTION

1. Field of the Invention

The present application relates generally to medical treatment systems, and more particularly, to a reduced pressure treatment system and method for applying reduced pressure to a tissue site.

2. Description of Related Art

Clinical studies and practice have shown that providing a reduced pressure in proximity to a tissue site augments and accelerates the growth of new tissue at the tissue site. The applications of this phenomenon are numerous, but one particular application of reduced pressure involves treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and micro-deformation of tissue at the wound site. Together these benefits result in increased development of granulation tissue and faster healing times. Typically, reduced pressure is applied by a reduced pressure source to tissue through a porous pad or other manifold device. In many instances, wound exudate and other liquids from the tissue site are collected within a canister to prevent the liquids from reaching the reduced pressure source.

SUMMARY

The problems presented by existing reduced pressure systems are solved by the, systems and methods of the illustrative embodiments described herein. In one embodiment, a system for applying reduced pressure to a subcutaneous tissue site is provided. The system includes a sleeve, which comprises a lumen, adapted for placement at a subcutaneous tissue site. The sleeve includes an opening. The system further includes a manifold sized and shaped to be inserted into the lumen of the sleeve. The manifold includes at least one aperture and is operable to deliver reduced pressure to the subcutaneous tissue site through the at least one aperture and the opening.

In another embodiment, an apparatus for applying reduced pressure to a subcutaneous tissue site includes a manifold having a distal end and a proximal end and a sleeve having a distal end and proximal end. The sleeve is sized and shaped for placement at the subcutaneous tissue site. The sleeve has an interior portion for receiving the manifold. The sleeve is formed with an opening operable to transfer reduced pressure from the manifold to the subcutaneous tissue site. The distal end of the manifold is sized and shaped to be inserted into the interior portion of the sleeve. The manifold is formed with at least one aperture and is operable to deliver reduced pressure to the subcutaneous tissue site through the at least one aperture.

In still another embodiment, a method for applying reduced pressure to a subcutaneous tissue site includes inserting a sleeve at the subcutaneous tissue site such that an opening on the sleeve is adjacent the subcutaneous tissue site. A manifold is inserted into the sleeve, the manifold including at least one aperture. Reduced pressure is supplied to the subcutaneous tissue site via the at least one aperture and the opening.

In yet another embodiment, a method of manufacturing an apparatus for applying reduced pressure to a subcutaneous tissue site is provided. The method includes forming a sleeve adapted for placement at the subcutaneous tissue site. The sleeve is further adapted to receive a manifold and includes an opening operable to transfer reduced pressure from the manifold to the subcutaneous tissue site.

Other objects, features, and advantages of the illustrative embodiments will become apparent with reference to the drawings and detailed description that follow.

DETAILED DESCRIPTION OF ILLUSTRATIVE EMBODIMENTS

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

Figure 1:
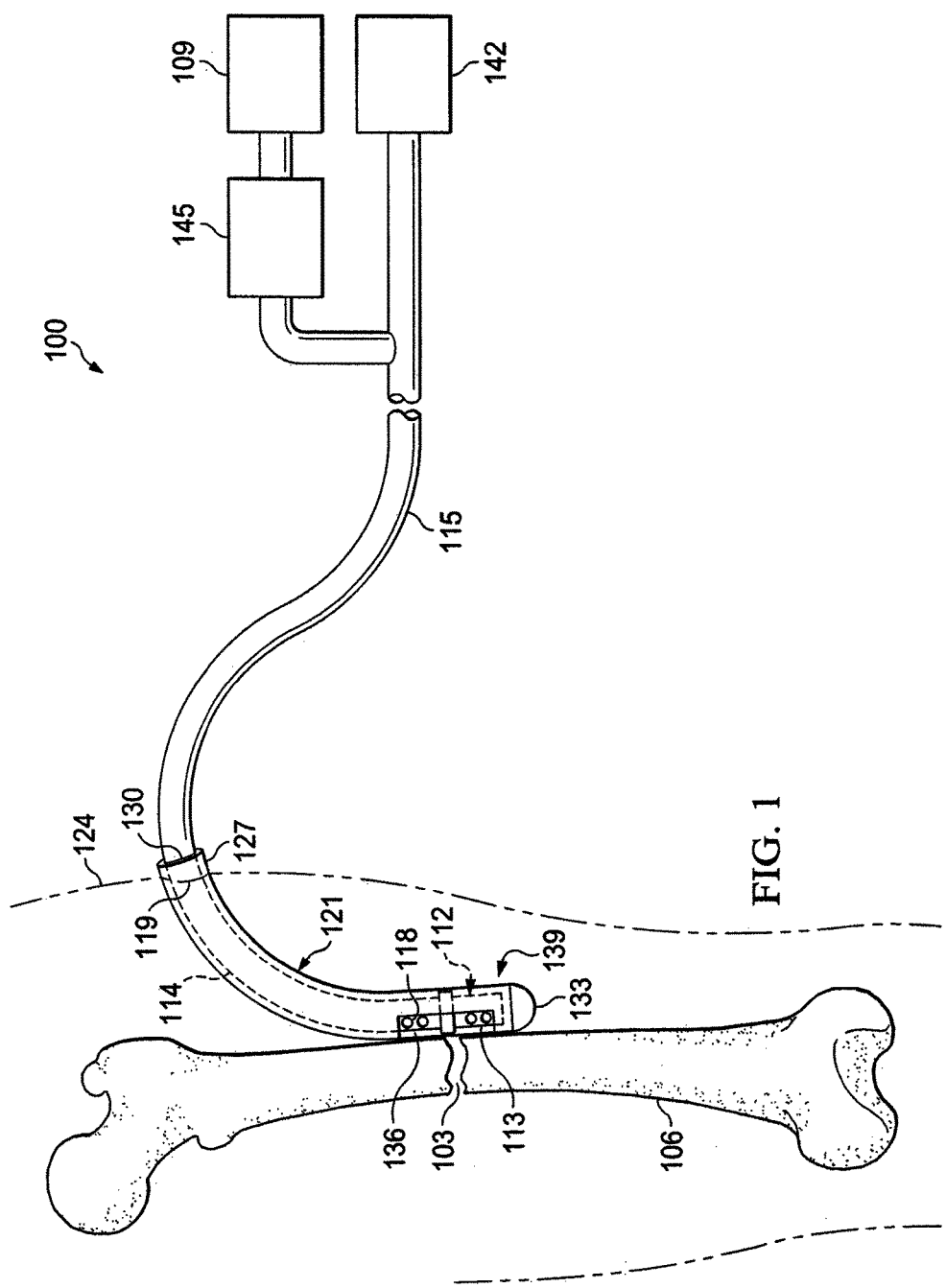
FIG. 1 illustrates a schematic of a reduced-pressure treatment system for applying reduced pressure to a subcutaneous tissue site according to an illustrative embodiment.

Referring to FIG. 1, a reduced-pressure treatment system 100, which applies reduced pressure to a tissue site 103, is shown according to an illustrative embodiment. In the embodiment illustrated in FIG. 1, the tissue site 103 is a bone tissue site. In particular, the tissue site 103 is a fracture on bone 106, which in the example illustrated is a femur. It is believed that reduced pressure at tissue site 103 provides a number of benefits. When used to promote bone tissue growth, reduced-pressure treatment can increase the rate of healing associated with a fracture, a non-union, a void, or other bone defects. Reduced-pressure treatment may also be used to improve recovery from osteomyelitis. The treatment may further be used to increase localized bone densities in patients suffering from osteoporosis. Finally, reduced-pressure treatment may be used to speed and improve osseointegration of orthopedic implants, such as hip implants, knee implants, and fixation devices.

While the tissue site 103 is bone tissue, the term "tissue site" as used herein may refer to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Referring to FIG. 1, a reduced pressure treatment system 100 includes a reduced pressure source 109 and a manifold 112 that is positioned at the tissue site 103. The reduced-pressure source 109 provides reduced pressure to tissue site 103 through the manifold 112. The manifold 112 may include a passageway (not illustrated in FIG. 1) for administering reduced pressure and removing or supplying fluids to the tissue site 103. The passageway may extend from a distal end 113 of the manifold 112 to a proximal end 114. The manifold 112 receives the reduced pressure from the reduced-pressure source 109 through a delivery conduit 115, which is in fluid communication with the manifold 112 and delivers reduced pressure to the manifold 112 during treatment. The manifold 112 may include at least one aperture, such as apertures 118, and may deliver reduced pressure to the tissue site 103 via the apertures 118.

In one illustrative embodiment, the manifold 112 may be inserted into a sleeve 121 to provide reduced pressure treatment to the tissue site 103. The sleeve 121, which may be a lumen member, may extend from the tissue site 103, through the patient's skin, and to a location external to the patient 124. The proximal end 127 of the sleeve 121, which has an opening 130 into which the manifold 112 may be inserted, may protrude from the patient 124 when the sleeve 121 is placed at the tissue site 103. Exposing the proximal end 127 of the sleeve 121 in this manner facilitates access to the sleeve 121 and the insertion of the manifold 112 into the sleeve 121. The manifold 112 has a longitudinal length L1, the sleeve has a longitudinal length L2, and a distance from the tissue site to a location external to the patient is L3. In one embodiment, L1>L2>L3. In another embodiment, the proximal end 127 of the sleeve 121 may be subcutaneously disposed in the patient 124, i.e., L2<L3. The sleeve 121 may be disposed at the tissue site 103 of a patient 124 in a variety of different spatial orientations, including the flexed orientation shown in FIG. 1. The sleeve 121 may be releasably secured to a patient 124 to hold the sleeve 121 in a fixed position with respect to the tissue site 103 or may be unsecured. In one embodiment, the sleeve 121 may be sutured into place or adhered using a medical epoxy, medical tape, or other means. The proximal end 127 may include a flange (not shown) to prevent the proximal end 127 from entering the patient 124. Moreover, the flange might be put in a position abutting an external portion of the patient 124 and adhered using epoxy, medical tape, sutures, etc.

Figure 9:
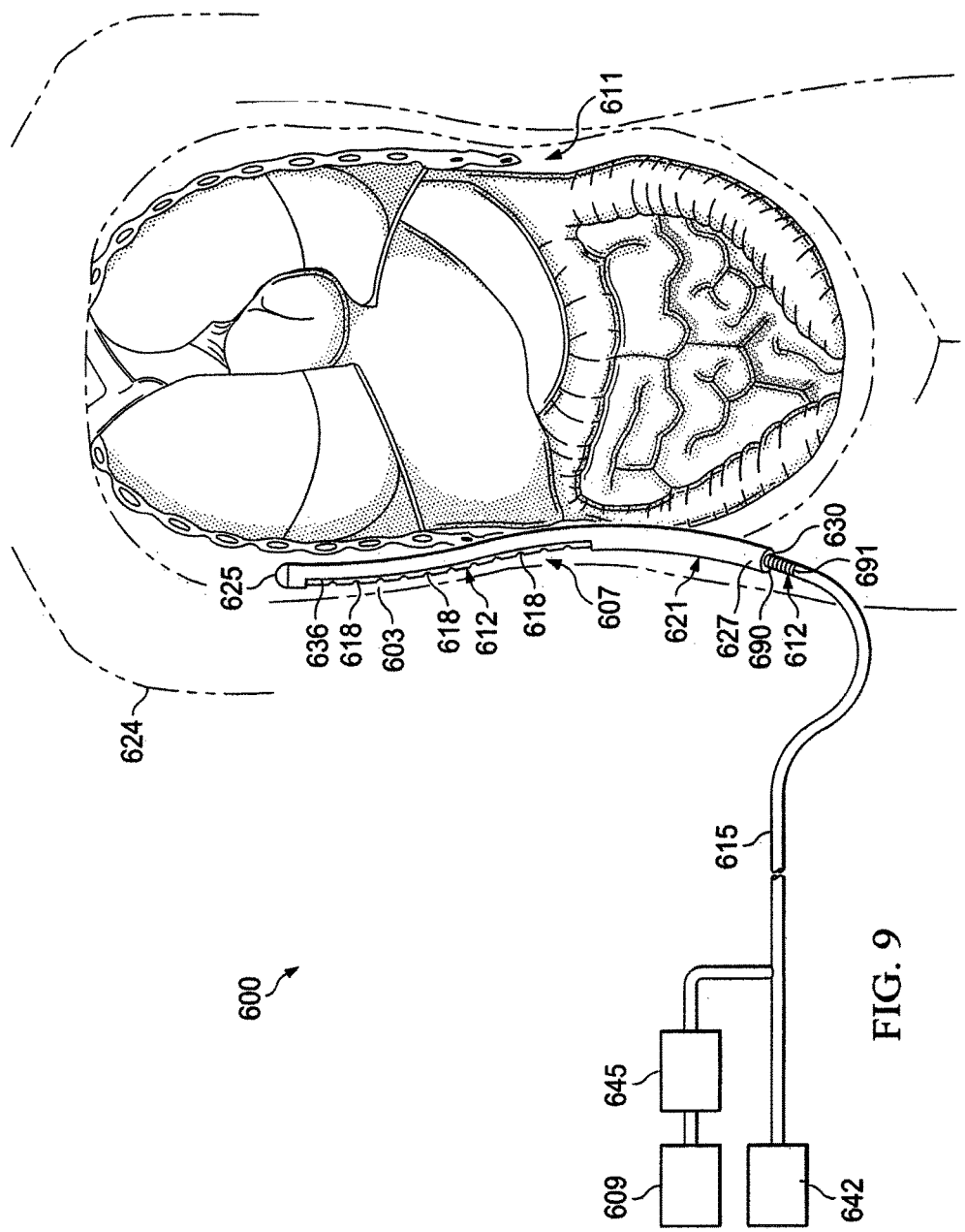
FIG. 9 illustrates a schematic of a reduced-pressure treatment system for applying reduced pressure to a tissue site in an abdominal cavity.

The sleeve 121 is capable of slidably receiving the manifold 112. The manifold 112 may be inserted into the opening 130 and moved toward the distal end 133 of the sleeve 121. The manifold 112 may be placed adjacent an opening 136 in sleeve 121. The opening 136 may be located at a distal portion 139 of the sleeve 121, may run the length of the sleeve 121, or may take any shape or size. The manifold 112 may include visual indicia (see by analogy 691 in FIG. 9) to help gauge the extent to which manifold 112 has been inserted into an interior portion of the sleeve 121. An exterior portion of the manifold 112 or the interior portion of the sleeve 121 or both may include ribs to provide tactile feedback to the healthcare provider regarding the relative position of the sleeve 121 and the manifold 111. The manifold 112 is capable of delivering reduced pressure from the reduced-pressure source 109 to the tissue site 103 via the opening 136 in the sleeve 121.

In use, it may be desirable to releasably secure the manifold 112 to the sleeve 121. An interference fit or groove lock may be used as described further below. Alternatively, the manifold 112 may include a longitudinal ridge member (not shown) that is positioned along the length (or a portion of the length) of the manifold 112 and that mates with a longitudinal groove (not shown) on the interior portion of the sleeve 121. Alternatively, the groove may be on the manifold 112 and the ridge member on the sleeve 121. This approach to securing the manifold 112 and sleeve 121 may further help assure that the manifold 112 assumes a proper position with respect to opening 136 and ultimately tissue site 103.

The manifold 112 may be both insertable and removable from the sleeve 121 while the sleeve 121 remains at the tissue site 103. During use, a pneumatic seal may be formed about the manifold 112 and sleeve 121 proximate an opening 119 in the patient 124, e.g., an opening in the patient's skin. The pneumatic seal may be formed using a drape material, medical tape, a hydrocolloid, or other sealing members.

The manifold 112 may be moved out of the sleeve 121 at any time. By allowing the manifold 112 to be inserted and removed from the sleeve 121 while the sleeve remains at the tissue site 103, the system 100 facilitates effective reduced-pressure treatment of the tissue site 103. For example, in the event that the manifold 112 becomes clogged, such as by fibrin, tissue, or any other bodily substance, the manifold 112 may be removed from the sleeve 121 and either cleaned or replaced with another manifold that can be inserted into the sleeve 121. Indeed, the manifold 112 may be removed or re-inserted for any reason, such as to visually monitor the integrity of the manifold 112 or to facilitate the movement of the patient 124 by disconnecting the patient 124 from the reduced-pressure source 109. Further, the insertion and removal of the manifold 112 may be repeated any number of times while minimizing the disruption of or damage to tissue in and around the tissue site 103 or at the skin.

In one embodiment, clogging of the manifold 112 may be reduced or prevented by delivering a purging fluid to the manifold 112. In this embodiment, a fluid source 142 may supply a purging fluid. The delivery conduit 115 may deliver the fluid to the manifold 112. The fluid may be a liquid or a gas, such as air, and may purge any blockages in the manifold 112. These purged substances, which may include fibrin, tissue, or any other bodily substance, are drawn out of the manifold 112 and toward the reduced-pressure source 109 using reduced pressure from the reduced-pressure source 109. These substances may be received by a container 145. In another embodiment, the fluid source 142 may also supply antibacterial agents, antiviral agents, cell-growth promotion agents, irrigation fluids, or other chemically active agents to the tissue site 103.

In one embodiment, a method for applying reduced pressure to the tissue site 103 includes inserting the sleeve 121 at the tissue site 103 such that the opening 136 on the sleeve 121 is adjacent the tissue site 103. The method may also include inserting the manifold 112, which includes apertures 118, into the sleeve 121. Reduced pressure is supplied to the tissue site 103 via the apertures 118 and the opening 136. The method may further include removing the manifold 112 from the sleeve 121. In this embodiment, the sleeve 121 may remain at the tissue site 103, and the manifold 112, or any other manifold, may be inserted or re-inserted into the sleeve 121. The sleeve 121 may also be removed from the tissue site 103 at any time, with or without the manifold 112 being positioned in the sleeve 121.

In one embodiment, a method of manufacturing an apparatus for applying reduced pressure to the tissue site 103 includes forming the sleeve 121. The method may also include forming the manifold 112.

Figure 2:
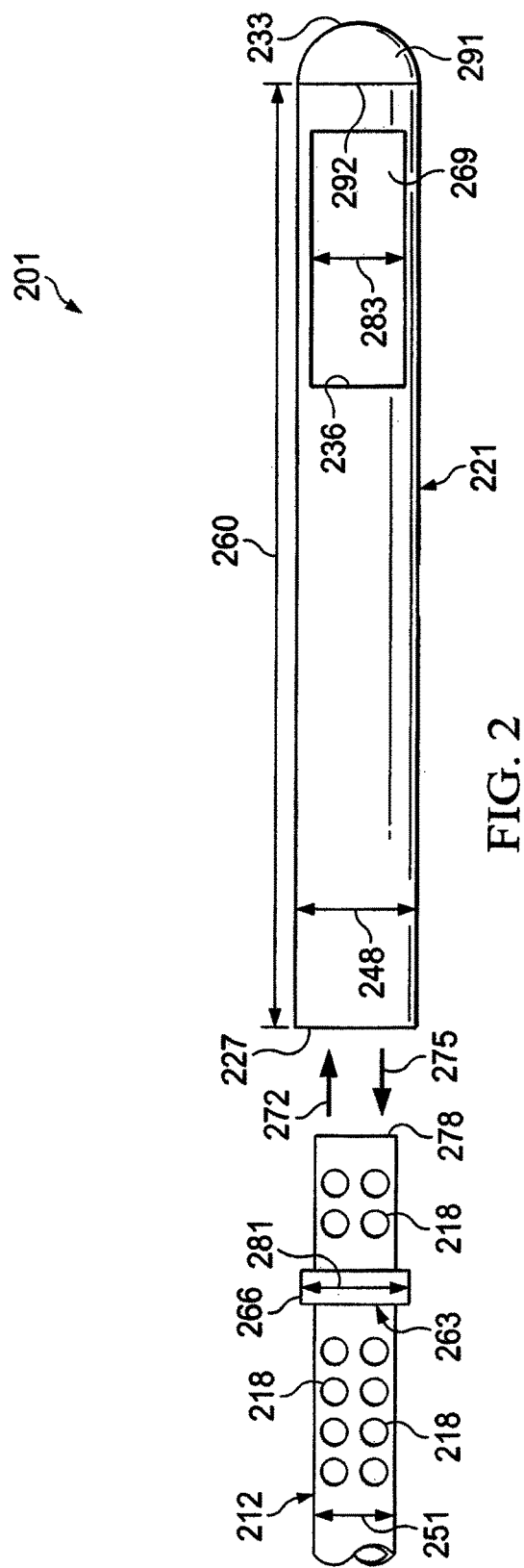
FIG. 2 illustrates a side view of an apparatus for applying reduced pressure to a subcutaneous tissue site according to an illustrative embodiment.
Figure 3:
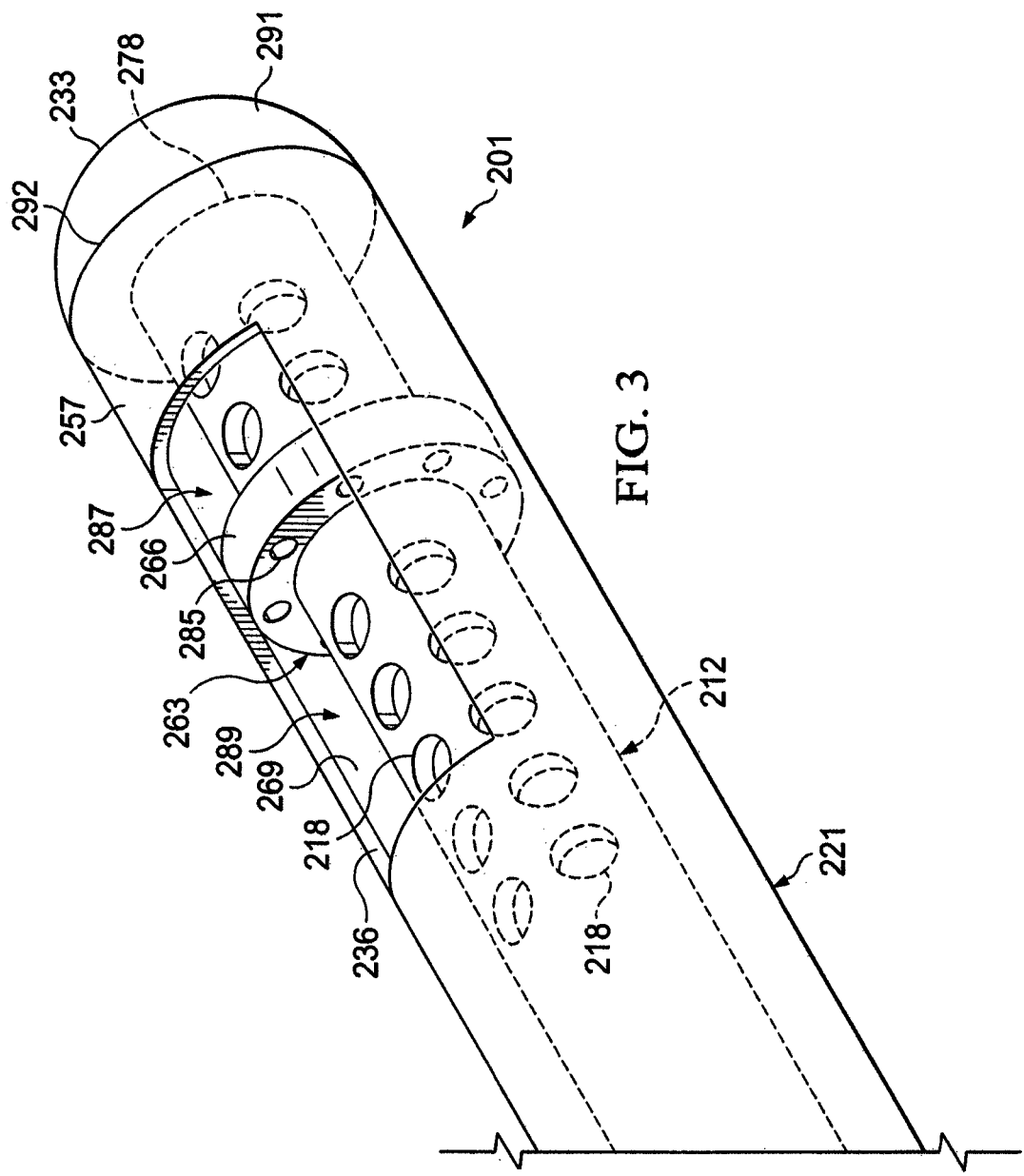
FIG. 3 illustrates a perspective view of a distal portion of the apparatus of FIG. 2 with a portion of the apparatus shown in hidden lines.
Figure 4:
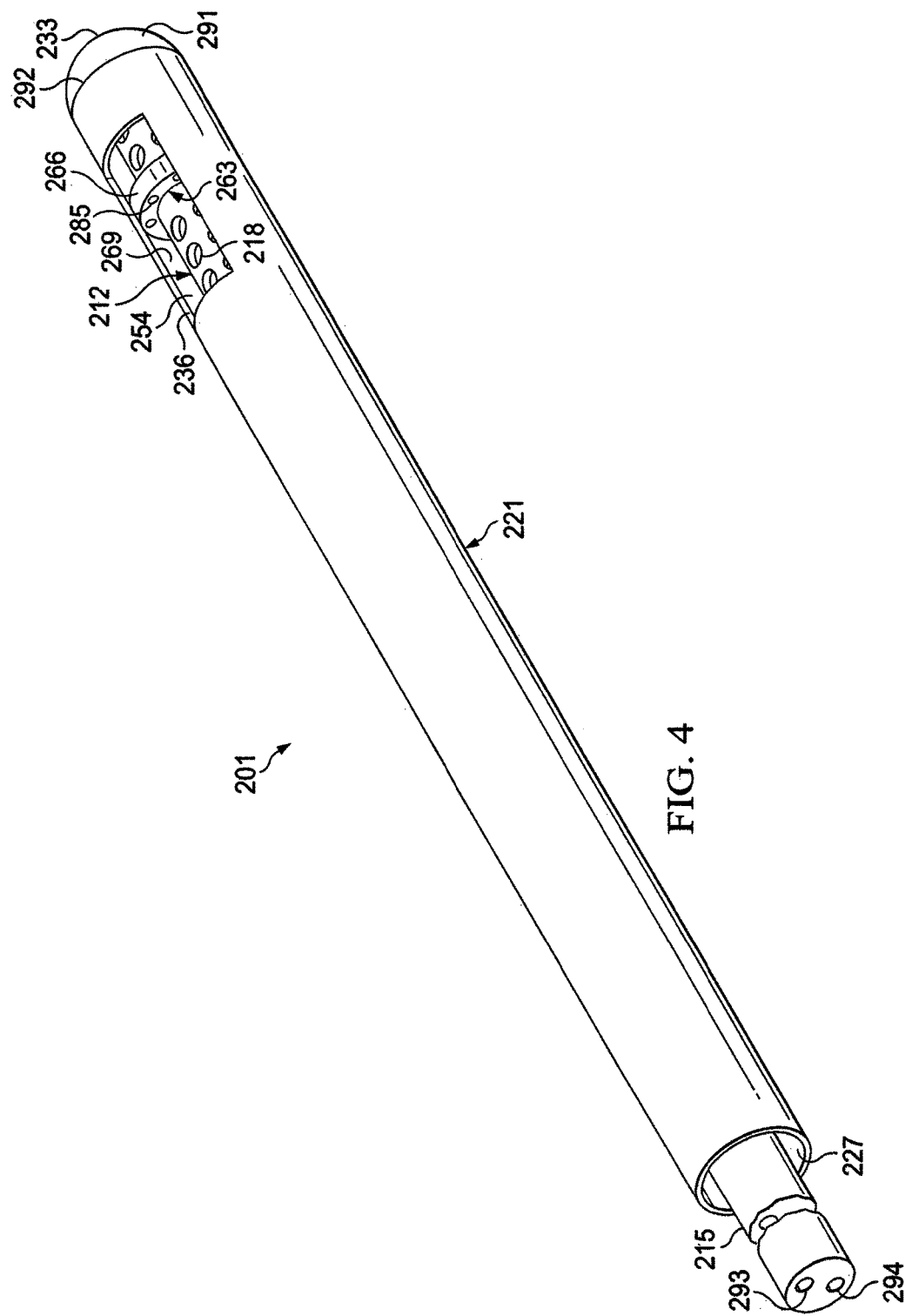
FIG. 4 illustrates a perspective view of the apparatus of FIG. 2.
Figure 5:
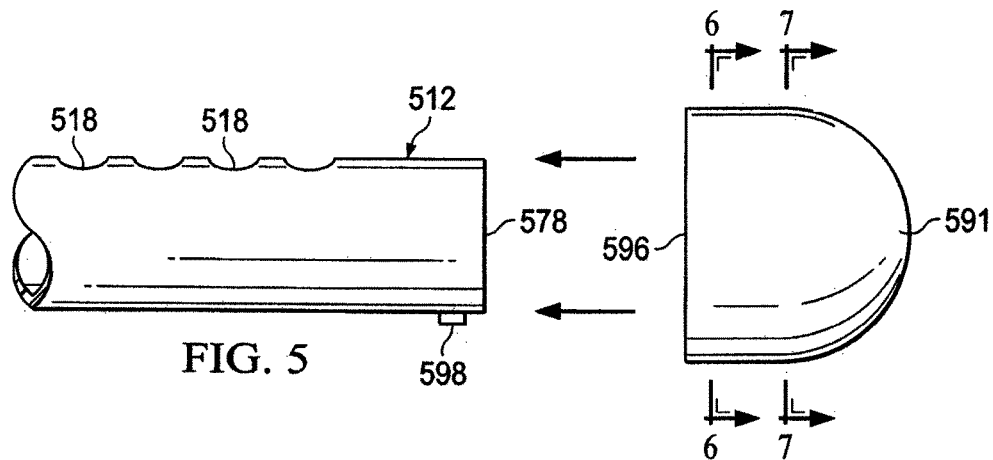
FIG. 5 illustrates a side view of a manifold and end cap according to an illustrative embodiment.
Figure 6:
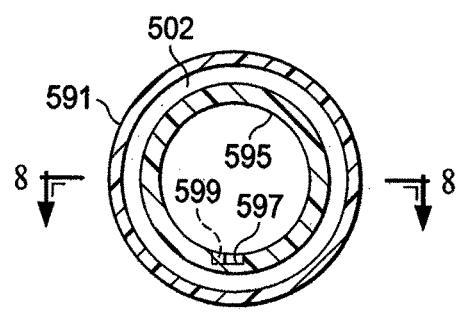
FIG. 6 illustrates a cross-sectional front view of the end cap of FIG. 5 taken at 6-6.
Figure 7:
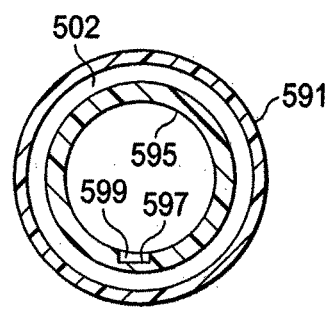
FIG. 7 illustrates a cross-sectional front view of the end cap of FIG. 5 taken at 7-7.
Figure 8:
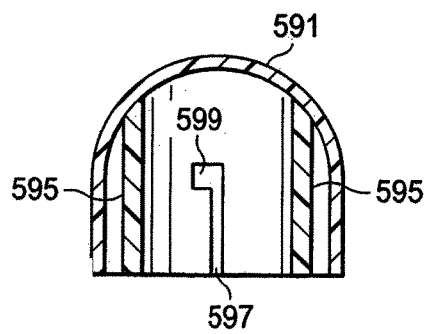
FIG. 8 illustrates a cross-sectional view of a portion of the end cap of FIG. 6 taken at 8-8.

Referring to FIGS. 2-4, an apparatus 201 for applying reduced pressure to a subcutaneous tissue site is shown in accordance with an illustrative embodiment. In particular, FIGS. 2-4 show a manifold 212 and a sleeve 221, which are similar to the manifold 112 and the sleeve 121 in FIG. 1, respectively. The sleeve 221 and the manifold 212 may have the same lateral cross-sectional shape. In FIGS. 2-4, the sleeve 221 and the manifold 212 have a circular lateral cross-section. The sleeve 221 or the manifold 212 may have other lateral cross-sectional shapes, such as an ellipse, a polygon, an irregular shape, or a customized shape.

The width 248 of the sleeve 221 is preferably larger than the width 251 of the manifold 212. However, the width 251 of the manifold 212 is not required to be constant along the entire length of the manifold 219. The width 251 of the manifold 212 may instead be varied along its length relative to the width 248 of the sleeve 221 to increase or decrease the amount of space between the manifold 212 and the sleeve 221.

The sleeve 221 or the manifold 212 may be made from a variety of biocompatible materials, including silicone. The sleeve 221 may be flexible such that the sleeve 221 is bendable when inserted or disposed subcutaneously. In one embodiment, the sleeve 221 is composed of a more flexible material than the manifold 212. The rigidity of the manifold 212 may help to prevent the collapse of the manifold 212 when exposed to reduced pressure.

The opening 236 of the sleeve 221, which is functionally analogous to the opening 136 in FIG. 1, may be located on a wall 257, or side wall, of the sleeve 221. The opening 236 is positioned at or near the most distal portion 233 of sleeve 221 and expands along a length of the sleeve 221. The opening 236 is capable of transferring reduced pressure from the manifold 212 to a tissue site. In one embodiment, the opening 236 may extend along substantially the entire length 260 of the sleeve 221.

The opening 236 is shown to have a substantially rectangular shape. However, the opening 236 may have any shape, including a circular, elliptical, polygonal, irregular, or customized shape. In the example in which the opening 236 has a customized shape, the opening 236 may be created based on the particular implementation or tissue site being treated by the apparatus 201. In addition, sleeve 221 may have two or more openings 236. The two or more openings 236 may face the same or different directions. For example, two openings 236 may be located on opposite sides of the wall 257. In another example, the two openings 236 may be located on the same side of the wall 257, and may be aligned along the length 260 of the sleeve 221. The size, shape, and number of openings 236 may depend on the particular tissue site and type of treatment being implemented.

Manifold 212 includes a plurality of apertures 218 that partially or fully surround the manifold 212. In the example in which the apertures 218 fully surround the manifold 212 and the manifold 212 is substantially cylindrical, the apertures 218 may be located around the circumference of the manifold 212. In the example in which the apertures 218 partially surround the manifold 212, each of the apertures 218 may be disposed to substantially face toward the opening 236 when the manifold 212 is inserted in the sleeve 221.

The manifold 212 may also include a flange 263, which may partially or fully surround the manifold 212. An outer edge 266 of the flange 263 may at least partially abut an inner surface 269 of the sleeve 221 when the manifold 212 is inserted in the sleeve 221. Also, the outer edge 266 of the flange 263 may be slidable along the inner surface 269 of the sleeve 221 when the manifold 212 is inserted into the sleeve 221 in the direction of arrow 272 or removed in the direction of arrow 275. The flange 263 may disposed anywhere along the manifold 212, including the end 278 of the manifold 212. Any number of flanges 263, such as two or more flanges 263 may be included.

The flange 263 is capable of moving a substance, such as a bodily substance or fluid, toward the proximal end 227 of the sleeve 221 when the manifold 212 is removed from the sleeve 221 as suggested by arrow 275 in FIG. 2. In this embodiment, the removal of the manifold 212 helps to clear the sleeve 221, including the distal end 239 of the sleeve 221, of debris, such as exudate, tissue, or any other substance.

The width 281, or outer diameter, of the flange 263 may be larger than the width 283 of the opening 236. In this embodiment, the flange 263 may help to prevent the manifold 212 from exiting the sleeve 221 through the opening 236, especially when the manifold 212 is being inserted into the sleeve 221. In an alternative embodiment (not shown), the interior of the sleeve 221 may including a blocking member designed to engage flange 263 and stop further insertion of manifold 212 into sleeve 221. Alternatively, the manifold 212 may include a surface feature on a proximal portion that prevents further advancement of the manifold 212 into sleeve 221.

In one embodiment, the flange 263 includes at least one hole, such as holes 285. The holes 285 allow fluid communication between the space 287 on the distal side of the flange 263 and the space 289 on the proximal side of the flange 263. The flange 263 may include any number of holes 285, and the holes 285 may have any shape. In one embodiment, the flange 263 has no holes 285. In another embodiment, the holes 285 may have one-way valves in the holes 285 that allow fluid to be pulled out of the sleeve 221 when the manifold 212 is removed, but avoid pushing air or other fluids when the manifold 212 is moved into the sleeve 221 (i.e., the valves allow fluid flow through the valves in the direction of arrow 275, but prevent flow in the direction of arrow 272).

Although the flange 263 is shown in FIG. 3 as being positioned along the length of opening 236 when the manifold 212 is fully inserted within the sleeve 221, the flange 263 could instead be located distal to the opening 236 when the manifold 212 is fully inserted. In this particular embodiment, the positioning of the flange 263 distal to the opening 236 may allow the flange 263 to better remove all bodily debris and substances (when the manifold is removed) that enter the sleeve 221 through the opening 236.

The sleeve 221 includes an end cap 291 that is coupled to a distal end 292 of the sleeve 221. As used herein, the term "coupled" includes coupling via a separate object, and also includes direct coupling. In the case of direct coupling, the two coupled objects touch each other in some way. The term "coupled" also encompasses two or more components that are continuous with one another by virtue of each of the components being formed from the same piece of material. Also, the term "coupled" includes chemical coupling, such as via a chemical bond. The term "coupled" may also include mechanical, thermal, or electrical coupling. "Coupled" may also mean fixedly coupled or removably coupled.

The end cap 291 may prevent fluid and reduced pressure from entering or exiting the sleeve 221 at the distal end 292 of the sleeve 221. The end cap 291 may have any shape, including a rounded or dome shape. In the example in which the end cap 291 has a rounded or dome shape, the shape of the end cap 291 better facilitates the subcutaneous insertion of the sleeve 221. Also, the space 293 inside the end cap 291 may be either hollow or solid. In another embodiment, the sleeve 221 does not include the end cap 291.

Referring more specifically to FIG. 4, a delivery conduit 215, which is functionally analogous to the delivery conduit 115 in FIG. 1, may deliver reduced pressure or fluid to the manifold 212. In one embodiment, the delivery conduit 215 may include two or more lumens, such as lumens 293 and 294. In one example, the lumen 293 delivers reduced pressure to the manifold 212, and the lumen 294 delivers a fluid to the manifold 212. The delivery conduit 215 is fluidly coupled to the manifold 212.

Referring to FIGS. 5-8, a manifold 512, which is similar to the manifold 112 in FIG. 1, and an end cap 591, which is similar to the end cap 291 in FIGS. 2-4, are shown in an exploded view. The sleeve to which end cap 591 is coupled is not illustrated in FIG. 5 for purposes of clarity. The end cap 591 includes a securing wall 595 on a sleeve-facing side 596 of the end cap 591. In one embodiment, the securing wall 595 receives the distal end 578 of the manifold 512 such that the securing wall 595 at least partially surrounds the distal end 578 of the manifold 512 and may form an interference fit. Alternatively, the distal end 578 of the manifold may receive and surround the securing wall 595 and may form an interference fit. The securing wall 595 may stabilize, secure, or prevent relative movement, e.g., lateral or longitudinal movement, of the manifold 512 and sleeve 521 when the manifold 512 is inserted into the sleeve 521. The space 502 around the securing wall 595 may be hollow or solid. The end cap 591 may be dome-shaped as shown or may be cylindrical, or may take any other shape.

In one embodiment, the securing wall 595 may include at least one groove, such as groove 597, and the manifold 512 may include at least one projection, such as projection 598, at or near the distal end 578 of the manifold 512. The projection 598 radially extends from the manifold 512. When the distal end 578 is inserted into the securing wall 595, the groove 597 slidably receives the projection 598. By inserting the projection 598 into the groove 597, the manifold 512 is substantially prevented from rotational movement with respect to with respect to the manifold 512. When the groove 597 slidably receives the projection 598, the manifold is oriented such that the apertures 518 may face the opening (not shown) in the sleeve. By moving the projection 598 into a locking portion 599 of the groove 597, the movement of the manifold 512 out of the sleeve may be hindered or prevented. In another embodiment, the groove 597 does not include the locking portion 599.

The illustrative embodiments of sleeves and manifolds may be used to provide reduced pressure treatment to one or more tissue sites and at tissue sites located at various locations within a patient. For example, the system 100 in FIG. 1 is shown applied to a tissue site 103 that is a bone. In another illustrative embodiment illustrated in FIG. 9, a reduced-pressure treatment system 600 is capable of providing reduced pressure to an abdominal tissue site 603.

The system 600 is analogous to system 100, and similar parts to those in FIG. 1 have been shown with reference numerals indexed by 500. The tissue site 603 is within an abdominal cavity and in particular within a paracolic gutter 607 of a patient 624. A manifold 612 is inserted into a sleeve 621. The sleeve 621 has a distal end 625 and a proximal end 627. The proximal end 627 of the sleeve 621 has an opening 630 into which the manifold 612 may be inserted. In this embodiment, there is no tissue defect as such, and the manifold 612 is exposed to multiple tissues and tissue sites along an anatomic plane or region, in this case, the abdominal paracolic gutter 607. It should be noted that system 600 is shown applied to one paracolic gutter 607, but may be applied bilaterally to provide reduced pressure treatment to a paracolic gutter 611 on the other side of the patient 624.

The sleeve 621 is inserted through an opening in the patient's abdomen and positioned in the paracolic gutter 607. The manifold 612 is inserted into the sleeve 621. The manifold 612 is positioned to have apertures 618 proximate opening 636 and proximate tissue site 603. The proximal end 690 of the manifold 612 is coupled to a delivery conduit 615. The delivery conduit 615 provides reduced pressure from a reduced pressure source 609 to remove fluids (e.g., ascites or exudates) from the tissue site 603, which are then are collected within a container 645. The delivery conduit 615 may also provide a fluid from a fluid source 642. The proximal end 690 of the manifold 612 may include visual indicia 691 to help the healthcare provider gauge the extent to which manifold 612 has been inserted into the sleeve 621. The proximal end 690 may also have a flange or other device to avoid over insertion of the manifold 612 into the sleeve 621.

The system 600 may be used to provide reduced pressure treatment at the wound site 603 or to only remove fluids, e.g., ascites, from the abdominal cavity. Numerous other tissue sites are also possible.

It should be apparent from the foregoing that an invention having significant advantages has been provided. While the invention is shown in only a few of its forms, it is not just limited but is susceptible to various changes and modifications without departing from the spirit thereof.

I claim:

1. A method for applying reduced pressure treatment to a subcutaneous tissue site, the method comprising:
   inserting a sleeve having a distal end and a proximal end at the subcutaneous tissue site such that an opening on the distal end of the sleeve is adjacent the subcutaneous tissue site;
   inserting a manifold having a distal end and a proximal end into the sleeve, wherein the manifold includes:
      a fluid passageway for delivering reduced pressure between the distal end and the proximal end, and
      a sidewall having at least one aperture and a flange substantially surrounding the sidewall of the manifold, wherein the flange forms a chamber between the at least one aperture and the opening, the flange having at least one hole allowing fluid communication between a distal side of the flange and a proximal side of the flange, when the distal end of the manifold is inserted into the sleeve and the at least one aperture is aligned with the opening, and wherein the flange is capable of extracting a substance from the proximal end of the sleeve when the distal end of the manifold is completely removed from the proximal end of the sleeve; and
   supplying reduced pressure to the subcutaneous tissue site via the at least one aperture, the chamber, and the opening.

2. The method of claim 1, wherein the sleeve further comprising the step of forming a pneumatic seal about the proximal end of the sleeve.

3. The method of claim 1, wherein the sleeve has a longitudinal groove and the manifold has a longitudinal ridge sized and shaped to slideably mate with the longitudinal groove, and wherein the step of inserting a manifold comprises placing the longitudinal ridge into the longitudinal groove and sliding the manifold into the sleeve.

4. The method of claim 1, wherein the sleeve is sized and shaped to stop the flange once the manifold has been inserted into the sleeve a predetermined distance.

5. The method of claim 1, wherein the manifold has a longitudinal length L1, the sleeve has a longitudinal length L2, and wherein L1>L2.

6. The method of claim 1, wherein the manifold has a longitudinal length L1, the sleeve has a longitudinal length L2, a distance from the tissue site to a location external to the patient is L3, and wherein L1>L2>L3.

7. The method of claim 1, wherein the tissue site is bone.

8. The method of claim 1, wherein the subcutaneous tissue site is within an abdominal cavity.

9. The method of claim 1, wherein the subcutaneous tissue site is proximate a paracolic gutter.

10. The method of claim 1, wherein the flange is disposed between a distal end of the manifold and the at least one aperture.

11. The method of claim 1, wherein the at least one aperture is disposed between the flange and a proximal end of the manifold.

12. A method for providing reduced pressure treatment to a tissue site, comprising:
   inserting a distal end of a sleeve subcutaneously through an opening in skin adjacent to the tissue site;
   positioning an opening in a sidewall of the sleeve adjacent to the tissue site;
   inserting a distal end of a manifold into a proximal end of the sleeve, wherein the manifold comprises:
      a fluid passageway for delivering reduced pressure between the distal end and a proximal end, and
      a flange substantially surrounding the sidewall of the manifold, the flange having at least one hole allowing fluid communication between a distal side of the flange and a proximal side of the flange, when the distal end of the manifold is inserted into the sleeve;
   aligning an aperture in a sidewall of the manifold with the opening in the sleeve adjacent to the tissue site, wherein the aperture and the opening are radially displaced by a chamber;
   sealing the manifold and the sleeve about the skin;
   providing reduced pressure treatment to the tissue site through the aperture in the manifold, the chamber, and the opening in the sleeve;
   removing the distal end of the manifold from the proximal end of the sleeve such that the manifold is completely removed from the sleeve; and
   reinserting the distal end of the manifold into the proximal end of the sleeve.

13. The method of claim 12, wherein the flange is disposed along the manifold between the distal end of the sleeve and the aperture in the manifold.

14. The method of claim 12, wherein the manifold comprises a plurality of apertures at least partially surrounding the manifold and each of the apertures is aligned with the opening.

15. The method of claim 12, wherein:
   the manifold comprises a plurality of apertures; and
   the flange is disposed along the manifold between at least two of the apertures.

16. The method of claim 12, further comprising supplying a fluid to the manifold to purge a blockage.

17. The method of claim 12, wherein the tissue site is bone.

18. The method of claim 12, wherein the tissue site is within an abdominal cavity.

19. The method of claim 11, wherein the tissue site is proximate a paracolic gutter.

20. A method for providing reduced pressure treatment to a tissue site, the method comprising:
   inserting a distal end of a sleeve subcutaneously to the tissue site;
   positioning an opening in the distal end of the sleeve sidewall adjacent to the tissue site;
   inserting a distal end of a manifold into a proximal end of the sleeve, wherein the manifold comprises:
      a fluid passageway for delivering reduced pressure between the distal end and the proximal end,
      a sidewall having at least one aperture and a flange disposed between the aperture and the distal end of the manifold, the flange having at least one hole allowing fluid communication between a distal side of the flange and a proximal side of the flange, when the distal end of the manifold is inserted into the sleeve;

aligning the aperture in the manifold with the opening in the sleeve adjacent to the tissue site, wherein the aperture and the opening are radially displaced by a chamber;

providing reduced pressure treatment to the tissue site through the aperture in the manifold, the chamber, and the opening in the sleeve; and removing the distal end of the manifold from the proximal end of the sleeve such that the flange is capable of extracting a substance from the proximal end of the sleeve when the manifold is completely removed from the sleeve.

\* \* \* \* \*